US010137186B2

United States Patent
Stinchcomb et al.

(10) Patent No.: US 10,137,186 B2
(45) Date of Patent: Nov. 27, 2018

(54) COMPOSITIONS AND METHODS FOR LIVE, ATTENUATED ALPHAVIRUS FORMULATIONS

(71) Applicant: TAKEDA VACCINES, INC., Cambridge, MA (US)

(72) Inventors: Dan T. Stinchcomb, Enumclaw, WA (US); Jill A. Livengood, Fort Collins, CO (US); Laszlo Varga, Fort Collins, CO (US)

(73) Assignee: Takeda Vaccines, Inc., Cambridge, MA (US)

( * ) Notice: Subject to any disclaimer, the term of this patent is extended or adjusted under 35 U.S.C. 154(b) by 0 days.

(21) Appl. No.: 14/209,921

(22) Filed: Mar. 13, 2014

(65) Prior Publication Data

US 2014/0271715 A1    Sep. 18, 2014

Related U.S. Application Data

(60) Provisional application No. 61/784,122, filed on Mar. 14, 2013.

(51) Int. Cl.
   *C12N 7/00*     (2006.01)
   *A61K 39/12*    (2006.01)
   (Continued)

(52) U.S. Cl.
   CPC .............. *A61K 39/12* (2013.01); *A61K 47/22* (2013.01); *A61K 47/26* (2013.01); *A61K 47/42* (2013.01);
   (Continued)

(58) Field of Classification Search
   None
   See application file for complete search history.

(56) References Cited

U.S. PATENT DOCUMENTS

| 4,338,335 A | * | 7/1982 | McAleer et al. ............. 514/777 |
| 5,545,555 A | | 8/1996 | Racioppi et al. |

(Continued)

FOREIGN PATENT DOCUMENTS

| CN | 101808657 A | 8/2010 |
| CN | 101835488 A | 9/2010 |

(Continued)

OTHER PUBLICATIONS

Weaver et al., "Chikungunya virus and prospects for a vaccine," Expert Rev. Vaccines 11(9): 1087-1101 (2012).*

(Continued)

*Primary Examiner* — Janet L Andres
*Assistant Examiner* — M Franco G Salvoza
(74) *Attorney, Agent, or Firm* — Honigman Miller Schwartz and Cohn LLP; Fernando Alberdi; Jonathan P. O'Brien

(57) ABSTRACT

Embodiments herein relate to compositions of and methods for live attenuated alphaviruses. In certain embodiments, a live, attenuated virus composition includes, but is not limited to, one or more live, attenuated alphaviruses and compositions to reduce inactivation and/or degradation of the live, attenuated alphavirus. In other embodiments, the live, attenuated virus composition may be a vaccine composition. In yet other compositions, a live, attenuated alphavirus composition may include HEPES buffer. In other embodiments, the HEPES buffer may further include a carbohydrate and gelatin and/or a salt.

15 Claims, 11 Drawing Sheets

(51) Int. Cl.
  *A61K 47/22* (2006.01)
  *A61K 47/26* (2006.01)
  *A61K 47/42* (2017.01)
  *A61K 39/00* (2006.01)

(52) U.S. Cl.
  CPC ............. *A61K 2039/5254* (2013.01); *C12N 2770/36134* (2013.01)

(56) References Cited

U.S. PATENT DOCUMENTS

| | | | |
|---|---|---|---|
| 6,458,560 B1* | 10/2002 | Dubensky, Jr. ...... | C07K 14/005 435/457 |
| 6,869,607 B1* | 3/2005 | Buschle et al. ............ | 424/184.1 |
| 6,982,088 B2* | 1/2006 | Francon et al. ........... | 424/204.1 |
| 2007/0148629 A1* | 6/2007 | Setiawan et al. ................. | 435/2 |
| 2009/0047255 A1* | 2/2009 | DePaz et al. ................ | 424/93.6 |
| 2011/0045025 A1 | 2/2011 | Middaugh et al. | |
| 2013/0022631 A1* | 1/2013 | Ella ........................ | A61K 39/12 424/186.1 |
| 2013/0243841 A1* | 9/2013 | Kommareddy et al. ...... | 424/422 |

FOREIGN PATENT DOCUMENTS

| | | | | |
|---|---|---|---|---|
| JP | 2005538939 A | | 12/2005 | |
| JP | 2007514450 A | | 6/2007 | |
| JP | 2012511321 A | | 5/2012 | |
| WO | WO 9617072 A2 | * | 6/1996 | ........... C07K 14/005 |
| WO | WO 9962500 A1 | * | 12/1999 | |
| WO | WO 0011201 A1 | * | 3/2000 | |
| WO | 2008026225 A2 | | 3/2008 | |
| WO | 2011090712 A2 | | 7/2011 | |
| WO | 2014151855 A1 | | 9/2014 | |

OTHER PUBLICATIONS

International Search Report and Written Opinion issued in PCT/US2014/026570, dated Jun. 27, 2014 pages.

\* cited by examiner

COMPOSITIONS AND METHODS FOR LIVE, ATTENUATED ALPHAVIRUS FORMULATIONS

PRIORITY

This US Non-Provisional Application claims priority to U.S. Provisional Application No. 61/784,122 filed Mar. 14, 2013. This provisional application is incorporated herein in its entirety by reference for all purposes.

GOVERNMENT FUNDING

This invention was made with Government support under grant R01AI093491 awarded by the National Institutes of Health. The Government has certain rights in this invention.

FIELD

Embodiments herein relate to compositions and methods for stabilizing live, attenuated viruses. Other embodiments relate to compositions and methods for reducing degradation of live, attenuated viruses. Still other embodiments relate to uses of these compositions in kits for portable applications and methods.

BACKGROUND

Vaccines to protect against viral infections have been effectively used to reduce the incidence of human or animal disease. One of the most successful technologies for viral vaccines is to immunize animals or humans with a weakened or attenuated strain of the virus (a "live, attenuated virus"). Due to limited replication after immunization, the attenuated strain does not cause disease. However, the limited viral replication is sufficient to express the full repertoire of viral antigens and generates potent and long-lasting immune responses to the virus. Thus, upon subsequent exposure to a pathogenic strain of the virus, the immunized individual is protected from disease. These live, attenuated viral vaccines are among the most successful vaccines used in public health.

The majority of viral vaccines approved for sale in the U.S. are live, attenuated viruses. Highly successful live viral vaccines include the yellow fever 17D virus, Sabin poliovirus types 1, 2 and 3, measles, mumps, rubella, varicella and vaccinia viruses. Use of the vaccinia virus vaccine to control smallpox outbreaks led to the first and only eradication of a human disease. The Sabin poliovirus vaccine has helped prevent crippling disease throughout the world and is being used in the efforts to eradicate polio. Childhood vaccination with measles, mumps, rubella and varicella vaccines prevent millions of deaths and illnesses internationally.

Chikungunya fever, a mosquito-borne viral disease that recently re-emerged to cause millions of cases of severe and often chronic arthralgia in Africa and Asia. Chikungunya has recently emerged in the Caribbean, demonstrating spread to the Western Hemisphere. Vaccines against this condition will not only prevent disease in endemic parts of the world, but will reduce the risk of importation into the U.S. and other parts of the Americas.

Recent technical advances, such as reassortment, reverse genetics and cold adaptation, have led to the licensure of live, attenuated viruses for influenza and rotavirus. A number of live, viral vaccines developed with recombinant DNA technologies are in animal and human clinical testing. These recombinant viral vaccines rely on manipulation of well-characterized attenuated viral vaccines. The safe, attenuated viruses are genetically engineered to express protective antigens for other viral or bacterial pathogens.

In order for live, attenuated viral vaccines to be effective, they must be capable of replicating after immunization. Thus, any factors that inactivate the virus can cripple the vaccine. In addition to freeze-drying, various additives have been identified that can help stabilize the viruses in live, attenuated viral vaccines (See for example Burke, Hsu et al 1999).

Other commonly used vaccines are sensitive to temperature extremes; either excessive heat or accidental freezing can inactivate the vaccine. Maintaining this "cold chain" throughout distribution is particularly difficult in the developing world. Thus, there remains a need for improving the stability of both existing and newly developed live, attenuated viral vaccine formulations.

SUMMARY

Embodiments herein concern methods and compositions to reduce or prevent deterioration or inactivation of live attenuated Alphavirus compositions. Certain compositions disclosed can include combinations of components that reduce deterioration of a live, attenuated alphaviruses. Other embodiments herein concern combinations of excipients that greatly enhance the stability of live, attenuated alphaviruses. Yet other compositions and methods herein are directed to reducing the need for lower temperatures (e.g. refrigerated or frozen storage) while increasing the shelf life of aqueous and/or reconstituted live attenuated, alphaviruses. In accordance with these embodiments, a live, attenuated alphavirus composition can be used to induce an immune response to the alphavirus in a subject wherein the subject can have a reduced incidence of infection caused by the alphavirus.

Some embodiments, directed to compositions, can include, but are not limited to, one or more live, attenuated alphaviruses, such as one or more live, attenuated alphavirus in combination with HEPES buffer, one or more carbohydrates and gelatin. In accordance with these embodiments, any HEPES buffer, and any gelatin product of use in a subject can be used in the composition. The sources of gelatin can vary from those derived from a mammalian origin to synthetically generated gelatin forms. Carbohydrates of use in the composition include but are not limited to sucrose, lactose galactose, trehalose, fructose, sorbitol, dextrose, mannitol and other carbohydrate sources. In certain embodiments, all three components are required to stabilize a live, attenuated alphavirus composition. In other embodiments, a salt can be added to the composition to provide salinity or osmolality to the composition (e.g. sodium chloride or other salt). In certain embodiments, a composition contemplated herein can include, but is not limited to, buffered HEPES about pH 6.0 to pH 10.0 at about 1 to 40 mM HEPES, one or more carbohydrate agents at about 1 to 25% w/v, and one or more protein agents that includes gelatin at about 0.01 to 5.0% w/v, wherein the composition decreases inactivation and/or degradation of a live, attenuated alphavirus.

Compositions contemplated herein can increase the stabilization and/or reduce the inactivation and/or degradation of a live, attenuated alphavirus including, but not limited to, chikungunya virus, o'nyong'nyong virus, Ross River virus, eastern equine encephalitis, Venezuelan Equine Encephalitis Virus and western equine encephalitis or other alphaviruses in the Coronaviridae and Togaviridae families. Other Semliki Forest virus complexes include, but are not limited to, Bebaru virus, Mayaro virus, Subtype: Una virus, O'Nyong Nyong virus: Subtype: Igbo-Ora virus, Ross River virus: Subtype: Bebaru virus; Subtype: Getah virus; Subtype: Sagiyama virus, Semliki Forest virus: Subtype: Me Tri virus.

Chikungunya virus is an alphavirus with a positive sense single-stranded RNA genome of approximately 11.6 kb. It is a member of the Semliki Forest Virus complex and is closely related to Ross River Virus, O'Nyong Nyong virus and Semliki Forest Virus. Compositions disclosed herein can be used for any member of the Semliki Forest Virus complex to increase stability or reduce degradation of a live, attenuated virus of use in vaccine compositions.

Human epithelial, endothelial, primary fibroblasts and monocyte-derived macrophages are permissive for chikungunya virus in vitro and viral replication is highly cytopathic but susceptible to type I and II interferon. In vivo, chikungunya virus appears to replicate in fibroblasts, skeletal muscle progenitor cells and myofibers Other embodiments concern live, attenuated virus compositions and methods directed to vaccine or immunogenic compositions capable of reducing or preventing onset of a medical condition caused by one or more of the alphaviruses contemplated herein. Pharmaceutical compositions disclosed herein concern compositions that are prepared for or formulated for introduction to a subject such as a human, an animal such as a domesticated animal or live-stock.

In certain embodiments, compositions contemplated herein can be partially or wholly dehydrated or hydrated. Further, compositions disclosed herein can be used during and after lyophilization of a live, attenuated alphavirus composition. In accordance with these embodiments, a composition may be 20% or more; 30% or more; 40% or more; 50% or more; 60% or more; 70% or more; 80% or more; or 90% or 95% or more dehydrated. Compositions described herein are capable of increasing the shelf life of an aqueous or rehydrated live attenuated alphavirus. Compositions disclosed herein increase stability of live, attenuated alphavirus at a wide-range of temperatures such as room temperature, sub-zero temperatures, elevated temperatures (e.g. −80° C.-37° C. and above) under lyophilized or liquid/frozen conditions. In certain embodiments, compositions disclosed herein can increase stability of a live, attenuated alphavirus 2 fold, 4 fold, 10 fold or more than a live, attenuated alphavirus composition not exposed to at least a composition of HEPES buffer, carbohydrate and gelatin.

Other embodiments concern methods for decreasing inactivation of a live, attenuated alphaviruses including, but not limited to, combining one or more live attenuated alphaviruses with a composition capable of reducing inactivation of a live, attenuated virus including, but not limited to, one or more protein agents; one or more saccharides or polyols agents; and one or more buffers, wherein the composition decreases inactivation of the live attenuated virus. In accordance with these embodiments, the live attenuated virus may include, but is not limited to, a Togavirus or Coronavirus, or in certain embodiments, any Alphavirus.

In certain embodiments, compositions contemplated herein are capable of decreasing inactivation and/or degradation of a hydrated live attenuated Alphavirus for greater than 12 to 24 hours at room temperatures (e.g. about 20° C. to about 25° C. or even as high as 37° C.) or refrigeration temperatures (e.g. about 0° to about 10° C.). In some embodiments, a combination composition is capable of maintaining about 100 percent of the live attenuated Alphavirus for greater than 24 hours. In addition, combination compositions contemplated herein are capable of reducing inactivation of a hydrated live attenuated virus during at least 2 freeze, at least 3, at least 4, at least 5, at least 6 and more thaw cycles. Other methods concern combination compositions capable of reducing inactivation of a hydrated live attenuated virus for about 24 hours to about 50 days at refrigeration temperatures (e.g. about 0° to about 10° C.). Compositions contemplated in these methods, can include, but are not limited to, a buffer, HEPES buffer, one or more carbohydrates such as sucrose or trehalose and one or more protein agents including gelatin. In certain embodiments, the live, attenuated virus composition remains at about 100% viral titer after greater than 20 hours at approximately 37° C. and about 100% viral titer after 50 days at refrigeration temperatures around 4° C. Other embodiments herein may include live, attenuated alphavirus composition remaining at about 90%, or about 80% viral titer after 7 days at approximately 21° C. and about 90%, or about 80% viral titer after 50 days at refrigeration temperatures around 4° C. Other embodiments contemplated include live, attenuated virus compositions remaining at about 3× to about 10× the concentration of viral titer after several hours (e.g. 20 hours) at approximately 37° C. compared to other compositions known in the art. (See for example, FIGS. 3 and 4). Compositions disclosed herein reduce degradation of the live, attenuated alphavirus when the composition is stored at approximately 37° C.

Other embodiments concern kits for decreasing the inactivation of a live, attenuated virus composition including, but not limited to, a container; and a composition including, but not limited to, buffered HEPES about pH 6.0 to pH 10.0 at about 1 to 30 mM HEPES, one or more carbohydrate agents (e.g. sucrose and/or trehalose) at about 1 to 25% w/v, and one or more protein agents that includes gelatin at about 0.01 to 5.0% w/v, wherein the composition decreases inactivation and/or degradation of a live, attenuated Alphavirus. In accordance with these embodiments, a kit may further include one or more live, attenuated alphaviruses. In other embodiments, a kit may further include a salt or salt solution (e.g. sodium chloride).

In other embodiments, compositions contemplated herein may contain trace amounts or no divalent cations. For example, compositions contemplated herein may have trace amounts or no calcium/magnesium ($Ca^{+2}/Mg^{+2}$).

BRIEF DESCRIPTION OF THE DRAWINGS

The following drawings form part of the instant specification and are included to further demonstrate certain aspects of particular embodiments herein. The embodiments may be better understood by reference to one or more of these drawings in combination with the detailed description presented herein.

DESCRIPTION OF ILLUSTRATIVE EMBODIMENTS

Definitions

Figure 1:
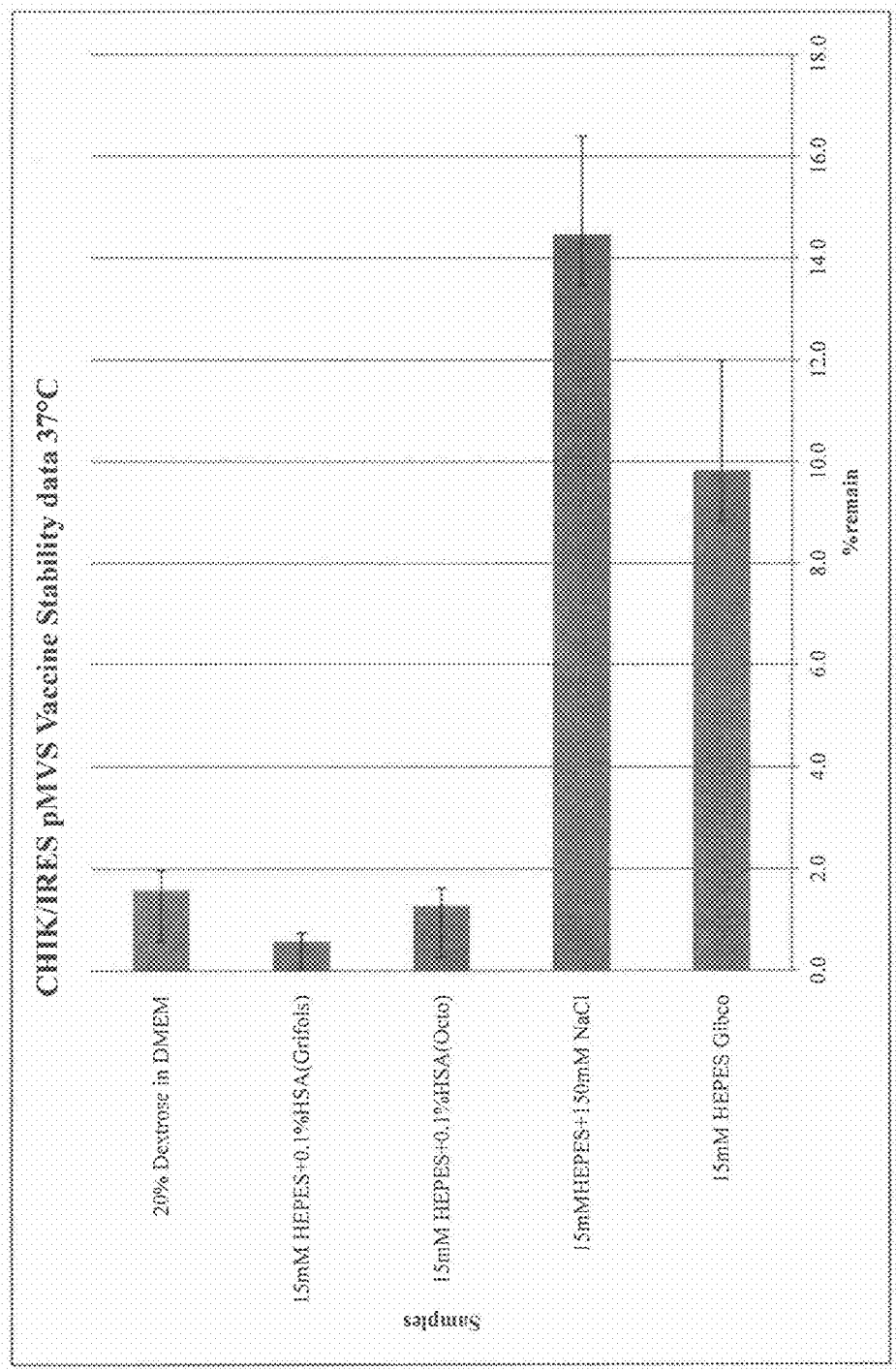
FIG. 1 represents an exemplary histogram of experiments using various compositions for testing the stability of exemplary attenuated Alphavirus compositions at 37° C.

As used herein, "a" or "an" may mean one or more than one of an item.

As used herein, "about" may mean up to and including plus or minus five percent, for example, about 100 may mean 95 and up to 105.

As used herein, "carbohydrate" agents can mean one or more monosaccharides, (e.g. glucose, galactose, ribose, mannose, rhamnose, talose, xylose, or allose arabinose.), one or more disaccharides (e.g. trehalose, sucrose, maltose, isomaltose, cellibiose, galactose gentiobiose, laminaribose, xylobiose, mannobiose, lactose, or fructose.), trisaccharides (e.g. acarbose, raffinose, melizitose, panose, or cellotriose) or sugar polymers (e.g. dextran, xanthan, pullulan, cyclodextrins, amylose, amylopectin, starch, celloologosaccharides, cellulose, maltooligosaccharides, glycogen, chitosan, or chitin).

As used herein CHIKV can mean Chikungunya Virus.

As used herein TCID50 can mean 50% Tissue Culture Infective Dose.

As used herein HB can mean HEPES Buffer Saline.

As used herein HBS can mean HEPES Buffer Saline+ Sucrose.

As used herein HSG can mean HEPES Buffer Saline+ Sucrose+Gelatin.

As used herein IRES can mean Internal Ribosomal Entry Site.

As used herein DMEM can mean Dulbecco's modified minimal essential medium.

As used herein MCT can mean Microcentrifuge Tubes.

As used herein PBS can mean Phosphate Buffered Saline.

As used herein FBS can mean Fetal Bovine Serum.

As used herein Pre-MVS can mean Pre-Master Virus Seed.

As used herein Lyo can mean lyophilized or dehydrated depending on the formulation of reference.

As uses herein gelatin can be a translucent, colorless, brittle (when dry), flavorless solid substance, derived from collagen obtained from various animal by-products or other. It is commonly used as a gelling agent and is commercially available. Any commercially available, isolated or synthetic gelatin agent is contemplated herein.

As used herein, "attenuated virus" can mean a virus that demonstrates reduced or no clinical signs of disease when administered to an animal.

DETAILED DESCRIPTIONS

In the following sections, various exemplary compositions and methods are described in order to detail various embodiments. It will be obvious to one skilled in the art that practicing the various embodiments does not require the employment of all or even some of the specific details outlined herein, but rather that concentrations, times and other specific details may be modified through routine experimentation. In some cases, well known methods or components have not been included in the description.

Stability of alphavirus vaccines has been assessed in certain embodiments disclosed herein. In certain embodiments, a formulation which confers significant protective effect from loss of titer of liquid, frozen, lyophilized and re-hydrated live, attenuated alphavirus formulations has been demonstrated. In certain embodiments, compositions disclosed herein concern a combination of two or more or all three components of HEPES buffer, one or more protein agents that include gelatin and one or more carbohydrate agents. In certain embodiments, a composition disclosed herein can include an alphavirus in a HEPES buffer, a carbohydrate that includes at least one of sucrose or trehalose and a gelatin derived from any source (e.g. pharmaceutical grade or a grade capable of being introduced to a subject). Certain compositions disclosed herein include salt or a salt solution. These formulations can be used for liquid, frozen or lyophilized storage of a live, attenuated alphavirus at about −80° C. to about 37° C. or above storage without significant loss of the CHIK vaccine. For example, long-term storage at 4° C. is also a possibility for this formulation.

Embodiments herein concern methods and compositions to reduce or prevent deterioration or inactivation of live attenuated Alphavirus compositions. Certain compositions disclosed can include combinations of components that reduce deterioration of a live attenuated virus. Other embodiments herein concern combinations of excipients that greatly enhance the stability of live attenuated viruses. Yet other compositions and methods herein are directed to reducing the need for lower temperatures (e.g. refrigerated or frozen storage) while increasing the shelf life of aqueous and/or reconstituted live attenuated alphavirus.

In accordance with these embodiments, certain live attenuated viruses are directed to alphaviruses. Some embodiments, directed to compositions, can include, but are not limited to, one or more live, attenuated alphaviruses, such as one or more live, attenuated alphavirus in combination with HEPES buffer, one or more carbohydrates and/or one or more protein agent that includes gelatin. In certain embodiments, alphavirus formulations disclosed herein include at least all three components. In other embodiments, a salt can be added in order to increase buffering capacity of the formulation.

Compositions contemplated herein can increase the stabilization and/or reduce the inactivation and/or degradation of a live attenuated alphavirus including, but not limited to, a live attenuated alphaviruses that include but are not limited to, chikungunya virus, o'nyong'nyong virus, Ross River virus, eastern equine encephalitis, Venezuelan Equine Encephalitis Virus and western equine encephalitis or other alphaviruses in the Coronaviridae and Togaviridae families.

Other embodiments concern live, attenuated virus compositions and methods directed to a vaccine compositions capable of reducing or preventing onset of a medical condition caused by one or more of the alphaviruses contemplated herein. In certain embodiments, a live, attenuated alphavirus is one that is incapable of replicating in mosquitoes. In other embodiments, a live, attenuated alphavirus contemplated herein is manipulated to be under eukaryotic control (e.g. insertion of an IRES sequence)

In certain embodiments, compositions contemplated herein can be partially or wholly dehydrated or hydrated. In other embodiments, carbohydrate agents contemplated of use in compositions herein can include, but are not limited to, sucrose, fructose, galactose and trehalose.

In certain embodiments, HEPES buffer is from about 1 mM to about 40 mM; a carbohydrate concentration is about 1 to about 25% w/v; and gelatin is about 0.01% to about 5%. In other embodiments, HEPES buffer is from about 1 mM to about 20 mM; a carbohydrate concentration is about 5 to about 20% w/v; and gelatin is about 0.1% to about 2%. In yet other embodiments, HEPES buffer is from about 5 mM to about 15 mM; a carbohydrate concentration is about 5 to about 25% w/v; and gelatin is about 0.5% to about 1.5%. In certain embodiments, formulations can further include 10-150 mM salt (e.g. sodium chloride or other appropriate salt known in the art). Other buffering agents can be used in certain compositions herein in combination with the required three components above.

Some embodiments herein concern partially or wholly dehydrated live, attenuated alphavirus compositions. In accordance with these embodiments, a composition may be 20% or more; 30% or more; 40% or more; 50% or more; 60% or more; 70% or more; 80% or more; or 90% or more dehydrated. In yet other embodiments, a composition disclosed herein can be a fully lyophilized composition.

Other embodiments concern methods for decreasing inactivation of a live attenuated alphaviruses including, but not limited to, combining one or more live attenuated alphaviruses with a composition capable of reducing inactivation of a live, attenuated alphavirus including, but not limited to, one or more protein agents; one or more carbohydrate, saccharides or polyols agents; and a HEPES buffer, wherein the composition decreases inactivation of the live, attenuated alphavirus. In accordance with these embodiments, the live attenuated virus may include, particular alphaviruses, such as those related to CHIK (e.g. Semliki Forest complex viruses).

Additionally, methods and compositions disclosed herein can include freeze drying or other dehydrating methods for the combination. In accordance with these methods and compositions, the methods and compositions decrease inactivation of the freeze dried or partially or wholly dehydrated live attenuated virus. In other methods, compositions for decreasing inactivation of a live attenuated virus may include an aqueous composition or may comprise a rehydrated composition after dehydration. Compositions described herein are capable of increasing the shelf life of an aqueous or rehydrated live attenuated alphavirus.

In certain embodiments, compositions contemplated herein are capable of decreasing inactivation and/or degradation of a hydrated live attenuated alphavirus for greater than 12 to 24 hours at room temperatures (e.g. about 20° C. to about 25° C. or even as high as 37° C.) or refrigeration temperatures (e.g. about 0° to about 10° C.). In some embodiments, a combination composition is capable of maintaining about 100 percent of the live attenuated Alphavirus for greater than 24 hours. In addition, combination compositions contemplated herein are capable of reducing inactivation of a hydrated live attenuated virus during at least 2 freeze and thaw cycles (or 3 or 4 or 5 etc.). Other methods concern combination compositions capable of reducing inactivation of a hydrated live attenuated virus for about 24 hours to more than 50 days at refrigeration temperatures (e.g. about 0° to about 10° C.). Compositions contemplated in these methods, can include, but are not limited to, a buffer, HEPES buffer, one or more carbohydrates such as sucrose or trehalose and one or more protein agents including gelatin. In certain embodiments, the live, attenuated virus composition remains at about 100% viral titer after greater than 20 hours at approximately 37° C. and about 100% viral titer after more than 50 days at refrigeration temperatures around 4° C. Other embodiments herein may include live, attenuated alphavirus composition remaining at about 90%, or about 80% viral titer after 7 days at approximately 21° C. and about 90%, or about 80% viral titer after 50 days at refrigeration temperatures around 4° C. Other embodiments contemplated include live, attenuated virus compositions remaining at about 3× to about 10× the concentration of viral titer after several hours (e.g. 20 hours) at approximately 37° C. compared to other compositions known in the art. (See the Example Section). Compositions disclosed herein reduce degradation of the live, attenuated alphavirus when the composition is stored at approximately 37° C. as well as other temperatures.

Other embodiments concern kits for decreasing the inactivation of a live, attenuated virus composition including, but not limited to, a container; and a composition including, but not limited to, buffered HEPES about pH 6.0 to pH 10.0, one or more carbohydrate agents (e.g. sucrose and/or trehalose), and one or more protein agents that includes gelatin, wherein the composition decreases inactivation and/or degradation of a live, attenuated Alphavirus. In accordance with these embodiments, a kit may further include one or more live, attenuated alphaviruses. buffered HEPES about pH 6.0 to pH 10.0 at about 1 to 40 mM HEPES, one or more carbohydrate agents at about 1 to 25% w/v, and one or more protein agents that includes gelatin at about 0.01 to 5.0% w/v, wherein the composition decreases inactivation and/or degradation of a live, attenuated alphavirus.

In other embodiments, compositions contemplated herein may contain trace amounts or no divalent cations. For example, compositions contemplated herein may have trace amounts or no calcium/magnesium ($Ca^{+2}/Mg^{+2}$).

No formulation for a live, attenuated Alphavirus vaccine has been identified that provides long term stability of lyophilized formulations at temperatures greater than 2-8° C. In addition, no formulation has been described that prevents loss of titer, stabilizes or reduces degradation of aqueous vaccines for greater than a few hours.

Formulations for other live, attenuated viruses have also been described (see for example Burke, Hsu et al. 1999). One common stabilizer, referred to as SPGA is a mixture of 2 to 10% sucrose, phosphate, potassium glutamate and 0.5 to 2% serum albumin (see for example Bovarnick, Miller et al. 1950). Various modifications of this basic formulation have been identified with different cations, with substitutions of starch hydrolysate or dextran for sucrose, and with substitutions of casein hydrolysate or poly-vinyl pyrrolidone for serum albumin. Other formulations use hydrolyzed gelatin instead of serum albumin as a protein source (Burke, Hsu et al 1999). However, gelatin can cause allergic reactions in immunized children and could be a cause of vaccine-related adverse events. U.S. Pat. No. 6,210,683 describes the substitution of recombinant human serum albumin for albumin purified from human serum in vaccine formulations.

Embodiments herein disclose compositions that enhance the stability of and/or reduce deterioration of live, attenuated virus vaccines compared to those in the prior art. Certain compositions disclosed herein provide stability of aqueous viruses for up to 2 hours; up to 3 hours; up to 4 hours and greater than 21 hours at or about 37° C. Certain compositions disclosed herein provide stability of aqueous viruses for up to 1 day to about 1 week or more, at or about room temperature (e.g. 25° C.). Embodiments contemplated herein provide increased protection of a live, attenuated virus from for example, freezing and/or thawing, and/or elevated temperatures. In certain embodiments, compositions herein can stabilize, reduce deterioration and/or prevent inactivation of dehydrated live, attenuated viral products in room temperature conditions (e.g. about 25° C.). In other embodiments, compositions contemplated herein can stabilize, reduce deterioration and/or prevent inactivation of aqueous live, attenuated viral products at about 25° C. or up to or about 37° C. Compositions and methods disclosed herein can facilitate the storage, distribution, delivery and administration of viral vaccines in developed and under developed regions.

Those skilled in the art will recognize that compositions or formulas herein relate to viruses that are attenuated by any means, including but not limited to, cell culture passage, reassortment, incorporation of mutations in infectious clones, reverse genetics, other recombinant DNA or RNA manipulation. In addition, those skilled in the art will recognize that other embodiments relate to viruses that are engineered to express any other proteins or RNA including, but not limited to, recombinant alphaviruses. Such viruses may be used as vaccines for infectious diseases, vaccines to treat oncological conditions, or viruses to introduce express proteins or RNA (e.g., gene therapy, antisense therapy, ribozyme therapy or small inhibitory RNA therapy) to treat disorders.

In some embodiments, compositions herein can contain one or more viruses with membrane envelopes (e.g., enveloped viruses) of the Togavirus, or Coronavirus, or any Alphavirus of the Togavirus family. In other embodiments, compositions herein can contain one or more enveloped, positive strand RNA virus of the Togavirus, or Coronavirus families. In certain embodiments, compositions can contain one or more live, attenuated alphavirus (e.g. Chikungunya) having one or more insertion, deletion or mutation to induce attenuation of the virus for use in a vaccine composition.

In certain embodiments, live attenuated alphavirus compositions can include one or more live attenuated Alphavirus constructs described in U.S. App No. PCT/US2009/000458, Filed Jan. 23, 2009 entitled: ATTENUATED RECOMBINANT ALPHAVIRUSES INCAPABLE OF REPLICATING IN MOSQUITOES AND USES THEREOF and U.S. patent application Ser. No. 12/804,535 filed Jul. 23, 2010, both applications and continuations and divisionals thereof are incorporated by reference for all purposes in their entirety.

Some embodiments herein relate to compositions for live, attenuated viruses in aqueous or lyophilized form. Those skilled in the art will recognize that formulations that improve thermal viral stability and prevent freeze-thaw inactivation will improve products that are liquid, powdered, freeze-dried or lyophilized and prepared by methods known in the art. After reconstitution, such stabilized vaccines can be administered by a variety routes, including, but not limited to intradermal administration, subcutaneous administration, intramuscular administration, intranasal administration, pulmonary administration or oral administration. A variety of devices are known in the art for delivery of the vaccine including, but not limited to, syringe and needle injection, bifurcated needle administration, administration by intradermal patches or pumps, intradermal needle-free jet delivery (intradermal etc), intradermal particle delivery, or aerosol powder delivery.

Embodiments can include compositions consisting of one or more live attenuated viruses (as described above) and a mixture of HEPES buffer or similar buffer; one or more carbohydrates and one or more proteins that include(s) gelatin. In certain embodiments, compositions include, but are not limited to one or more live attenuated alphaviruses, HEPES buffer or similar buffer; one or more of sucrose or trehalose and one or more proteins that include gelatin.

In some embodiments, the carbohydrate is a sugar or a polyol. Sugars can include, but are not limited to, monosaccharides, (e.g. glucose, galactose, ribose, mannose, rhamnose, talose, xylose or allose arabinose), disaccharides (e.g. trehalose, sucrose, maltose, isomaltose, cellibiose, gentiobiose, laminaribose, xylobiose, mannobiose, lactose, or fructose.), trisaccharides (e.g. acarbose, raffinose, melizitose, panose, or cellotriose) or sugar polymers (e.g. dextran, xanthan, pullulan, cyclodextrins, amylose, amylopectin, starch, celloologosaccharides, cellulose, maltooligosaccharides, glycogen, chitosan, or chitin). Polyols can include, but are not limited to, mannitol, sorbitol, arabitol, erythritol, maltitol, xylitol, glycitol, glycol, polyglycitol, polyethylene glycol, polypropylene glycol, and glycerol.

Anhydrobiotic organisms that can tolerate low water conditions contain large amounts of trehalose. Trehalose has been shown to prevent both membrane fusion events and phase transitions that can cause membrane destabilization during drying. Structural analysis suggests that trehalose fits well between the polar head groups in lipid bylayers. Trehalose also prevents denaturation of labile proteins during drying. It is thought that trehalose stabilizes proteins by hydrogen bonding with polar protein residues. Trehalose is a disaccharide consisting of two glucose molecules in a 1:1 linkage. Due to the 1:1 linkage, trehalose has little or no reducing power and is thus essentially non-reactive with amino acids and proteins. This lack of reducing activity may improve the stabilizing affect of trehalose on proteins. In certain embodiments, trehalose provides stability to live, attenuated viruses. This activity of trehalose may be due to its ability to stabilize both the membranes and coat proteins of the viruses.

In certain embodiments, compositions can be described that typically include a physiologically acceptable buffer. Those skilled in the art recognize that HEPES was found to have unexpected stabilizing effect on the alphavirus compositions disclosed herein. In addition, those skilled in the art recognize that adjusting salt concentrations to near physiological levels (e.g., saline or 0.15 M total salt) may be optimal for parenteral administration of compositions to prevent cellular damage and/or pain at the site of injection. Those skilled in the art also will recognize that as carbohydrate concentrations increase, salt concentrations can be decreased to maintain equivalent osmolarity to the formulation. In certain embodiments, a buffering media with pH greater than 6.8 to about pH 10.0 is contemplated; some live, attenuated viruses (e.g. alphaviruses) are unstable at low pH.

Some live, attenuated viral vaccine compositions herein concern compositions that increase stability and/or reduce deterioration of live, attenuated virus in addition to having reduced immunogenicity or are non-immunogenic.

Pharmaceutical Compositions

Embodiments herein provide for administration of compositions to subjects in a biologically compatible form suitable for pharmaceutical administration in vivo. By "biologically compatible form suitable for administration in vivo" is meant a form of the active agent (e.g. live, attenuated virus composition of the embodiments) to be administered in which any toxic effects are outweighed by the therapeutic effects of the active agent. Administration of a therapeutically active amount of the therapeutic compositions is defined as an amount effective, at dosages and for periods of time necessary to achieve a desired result. For example, a therapeutically active amount of a compound may vary according to factors such as the disease state, age, sex, and weight of the individual, and the ability formulations to elicit a desired response in the individual. Dosage regima may be adjusted to provide the optimum therapeutic response.

In some embodiments, composition (e.g. pharmaceutical chemical, protein, peptide of an embodiment) may be administered in a convenient manner such as subcutaneous, intravenous, by oral administration, inhalation, transdermal application, intravaginal application, topical application, intranasal or rectal administration. In a more particular embodiment, the compound may be orally or subcutaneously administered. In another embodiment, the compound may be administered intravenously. In one embodiment, the compound may be administered intranasally, such as inhalation.

A compound may be administered to a subject in an appropriate carrier or diluent, co-administered with the composition. The term "pharmaceutically acceptable carrier" as used herein is intended to include diluents such as saline and aqueous buffer solutions. The active agent may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use may be administered by means known in the art. For example, sterile aqueous solutions (where water soluble) or dispersions and sterile powders for the extemporaneous preparation of sterile injectable solutions or dispersion may be used. In all cases, the composition can be sterile and can be fluid to the extent that easy syringability exists. It may further be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants.

Sterile injectable solutions can be prepared by incorporating active compound in an amount with an appropriate solvent or with one or a combination of ingredients enumerated above, as required, followed by sterilization.

Upon formulation, solutions can be administered in a manner compatible with the dosage formulation and in such amount as is therapeutically effective. The formulations are easily administered in a variety of dosage forms, such as the type of injectable solutions described above. It is contemplated that slow release capsules, timed-release microparticles, and the like can also be employed for administering compositions herein. These particular aqueous solutions are especially suitable for intravenous, intramuscular, subcutaneous and intraperitoneal administration. In some embodiments, formulations disclosed herein can be administered before, during and/or after exposure to an alphavirus of the instant invention.

In another embodiment, nasal solutions or sprays, aerosols or inhalants may be used to deliver the compound of interest. Additional formulations that are suitable for other modes of administration include suppositories and pessaries. A rectal pessary or suppository may also be used.

Oral formulations include such normally employed excipients as, for example, pharmaceutical grades of mannitol, lactose, starch, magnesium stearate, sodium saccharine, cellulose, magnesium carbonate and the like. In certain embodiments, oral pharmaceutical compositions can include an inert diluent or assimilable edible carrier, or may be enclosed in hard or soft shell gelatin capsule, or may be compressed into tablets, or may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage can be obtained.

Kits

Further embodiments concerns kits for use with methods and compositions described herein. Compositions and live virus formulations may be provided in the kit. The kits can also include a suitable container, live, attenuated virus compositions detailed herein and optionally one or more additional agents such as other anti-viral agents, anti-fungal or anti-bacterial agents.

The kits may further include a suitably aliquoted composition of use in a subject in need thereof. In addition, compositions herein may be partially or wholly dehydrated or aqueous. Kits contemplated herein may be stored at room temperatures or at refrigerated temperatures as disclosed herein depending on the particular formulation.

The container means of the kits will generally include at least one vial, test tube, flask, bottle, syringe or other container means, into which a composition may be placed, and preferably, suitably aliquoted. Where an additional component is provided, the kit will also generally contain one or more additional containers into which this agent or component may be placed. Kits herein will also typically include a means for containing the agent, composition and any other reagent containers in close confinement for commercial sale. Such containers may include injection or blow-molded plastic containers into which the desired vials are retained.

EXAMPLES

The following examples are included to demonstrate certain embodiments presented herein. It should be appreciated by those of skill in the art that the techniques disclosed in the Examples which follow represent techniques discovered to function well in the practices disclosed herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope herein.

Example 1

Buffer Screen

In certain exemplary method, liquid composition and lyophilizable compositions suitable for preclinical and clinical testing and use of alphavirus vaccines are identified. One consideration regarding a liquid composition in accordance with these exemplary compositions is that some alphaviruses are pH sensitive (e.g. to low pH). Therefore, components of a compositions disclosed herein include careful considerations regarding pH. In certain exemplary compositions, the pH of the formulations was about pH 6 to about 10 with many formulations around pH 6.5 to 7.5 and up to around 9.5.

In some methods, attenuated Chikungunya Viruses (hereinafter CHIK) are used as an example of an alphavirus composition for pre-clinical and clinical testing. Compositions for these methods are provided. In one exemplary experiment, a predetermined amount of CHIK-IRES vaccine (pMVS) where this attenuated virus is under control of an IRES insertion. Any attenuated alphavirus can be used in these exemplary compositions to increase stability of the composition and reduce degradation. Initially, many different base buffers were tested such as DMEM, PBS, HEPES and others.

Certain tests were performed, such as incubation for up to 21 hours at 37° C. to test stability of the attenuated virus formulation. Samples were taken to titrate for the presence of infectious virus by $TCID_{50}$ in 96 well plates on Vero cells. A percentage of the remaining virus as compared to an input (un-incubated) vaccine control was calculated. Incubation of $10^5$ $TCID_{50}$ of the CHIK virus vaccine in compositions containing PBS alone, 20% DMEM or DMEM buffered Dextrose demonstrated a rapid loss in potency. Certain exemplary compositions were found to be effective at stabilizing attenuated alphaviruses such as CHIK virus vaccine, for example, a composition containing various concentrations of HEPES buffer (4-(2-hydroxyethyl)-1-piperazineethanesulfonic acid) (data not shown) such as about 1 to about 30 mM HEPES. In one example, a composition containing 150 mM NaCl and 15 mM HEPES (HEPES Buffer Saline—HS) was found to provide increased stability to the attenuated alphavirus vaccine compared to a control (FIG. 1).

Figure 2:
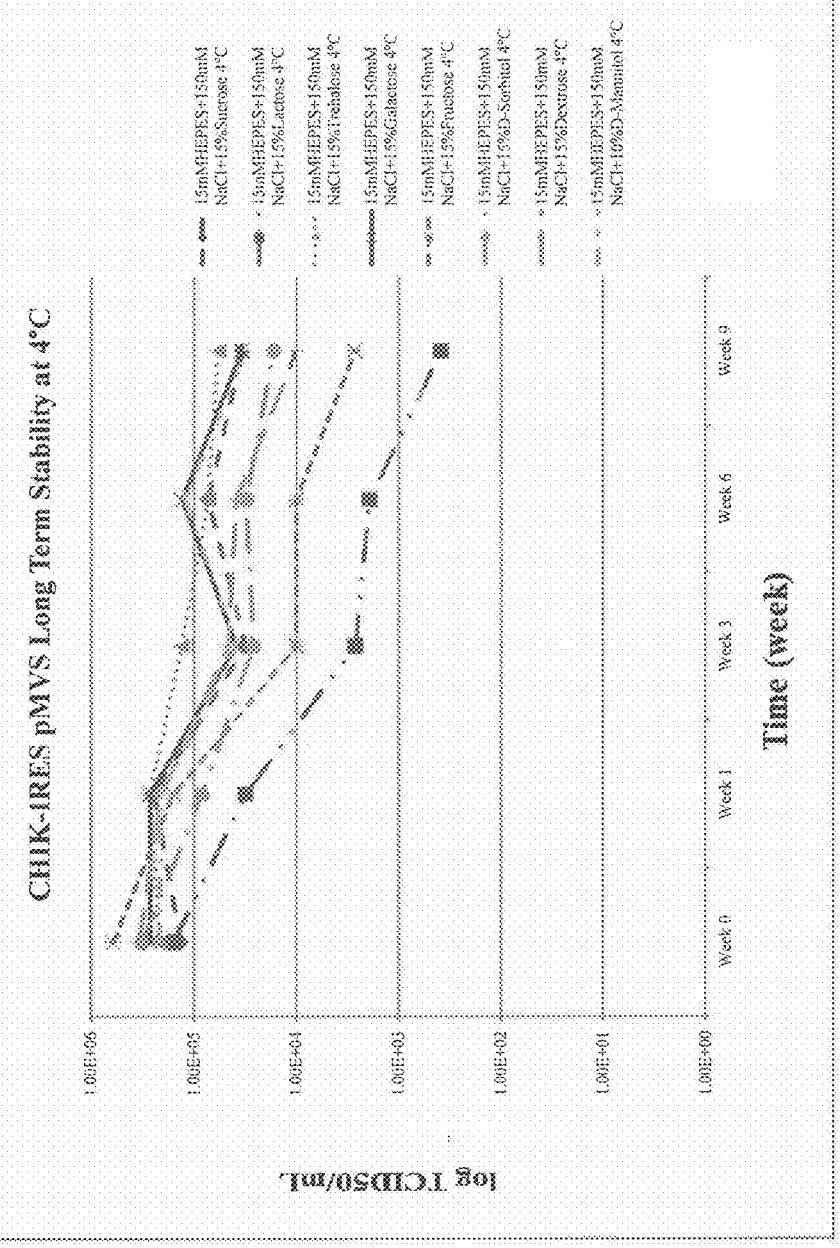
FIG. 2 represents an exemplary histogram of experiments using compositions having different carbohydrate agents for testing the stability of exemplary attenuated Alphavirus compositions at 4° C.

FIGS. 1 and 2 represent exemplary histograms illustrating potency (indicated as percentage of total virus remaining after the time period indicated) of the attenuated alphavirus, CHIKV, vaccine remaining after incubation in various compositions for ~21 hours at 37° C. Compositions containing different concentrations of HEPES increased stability of the CHIK vaccine significantly compared to other buffer compositions (20%-55% vs. less than 10%, data not shown). In FIG. 1, compositions containing 15 mM HEPES having 150 mM NaCl or 15 mM HEPES demonstrated significant affects on vaccine stability and potency compared to others.

Example 2

In some other exemplary methods, a long term stability experiment at 4° C. was performed to analyze effects of various carbohydrates (e.g. sugars) on alphavirus vaccine stability, for example the CHIK virus vaccine, based on observations that including one or more carbohydrates had a positive effect on CHIK vaccine stability. Compositions containing HEPES and a carbohydrate, such as sucrose, lactose, trehalose, galactose, fructose, D-sorbitol, Dextrose and D-Mannitol, were generated. Individual aliquots of a predetermined concentration of CHIK-IRES vaccine (pMVS) were formulated in these compositions, and incubated for over 12 weeks at 4° C. Samples were collected at time points indicated in FIG. 2 and titrated on Vero cells. As illustrated in FIG. 2, compositions of about 15% Trehalose; 15% Sucrose or 10% D-Manitol in combination with HEPES Buffered Saline (HB) demonstrated about an equal improvement in virus stability, better than other compositions.

Figure 3:
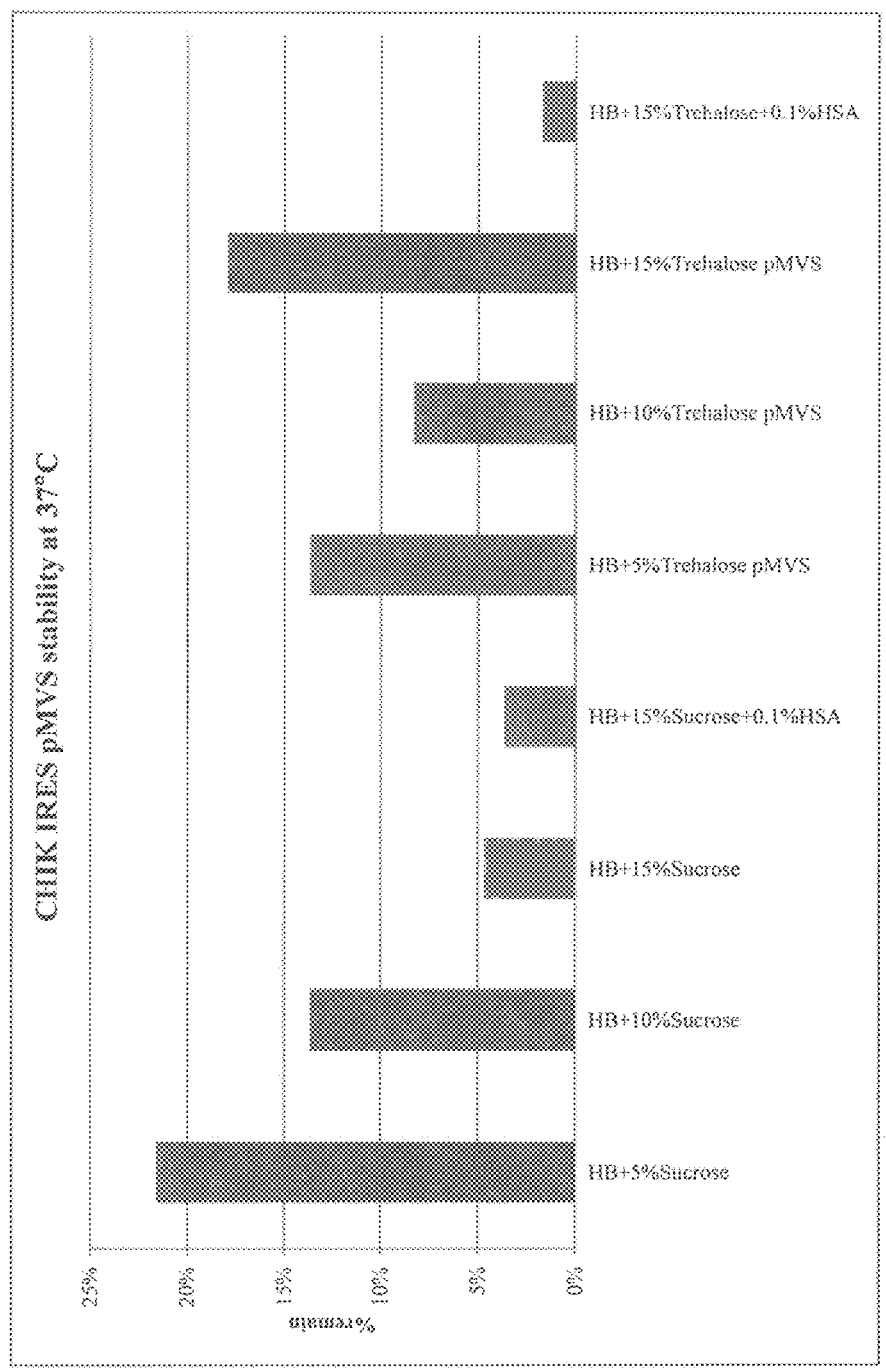
FIG. 3 represents an exemplary histogram of experiments using various compositions for testing the stability of exemplary attenuated Alphavirus compositions at 37° C.

In certain exemplary methods, formulations that included either sucrose or trehalose were examined for properties regarding increased stability of alphavirus vaccine and other formulations. In certain methods, $10^5$ $TCID_{50}$ of a CHIK virus vaccine was incubated in various compositions of HEPES buffer (HB) with increasing concentrations of sucrose or trehalose in the presence or absence of a protein at room temperature, 37° C., and analyzed for stability for up to 21 hours. As illustrated in the histogram plot in FIG. 3, compositions containing HEPES buffer with 5% sucrose (referred to as HBS) or HEPES buffer with 15% trehalose more stability than compositions of HEPES buffer and human serum albumin or at other carbohydrate concentrations.

FIG. 2 is an exemplary graph demonstrating stability of a liquid alphavirus composition, CHIKV vaccine composition containing HEPES buffered saline and various carbohydrates over 12 weeks at 4° C. FIG. 2 represents an exemplary histogram plot illustrating percentage of total virus remaining after an incubation in compositions containing HEPES buffer 150 mM NaCl and various concentrations of carbohydrates, e.g. sucrose or trehalose, in the presence or absence of 0.1% HSA for weeks at 4° C.

Example 3

Screening for Protein Induced Stability Formulations

Figure 4:
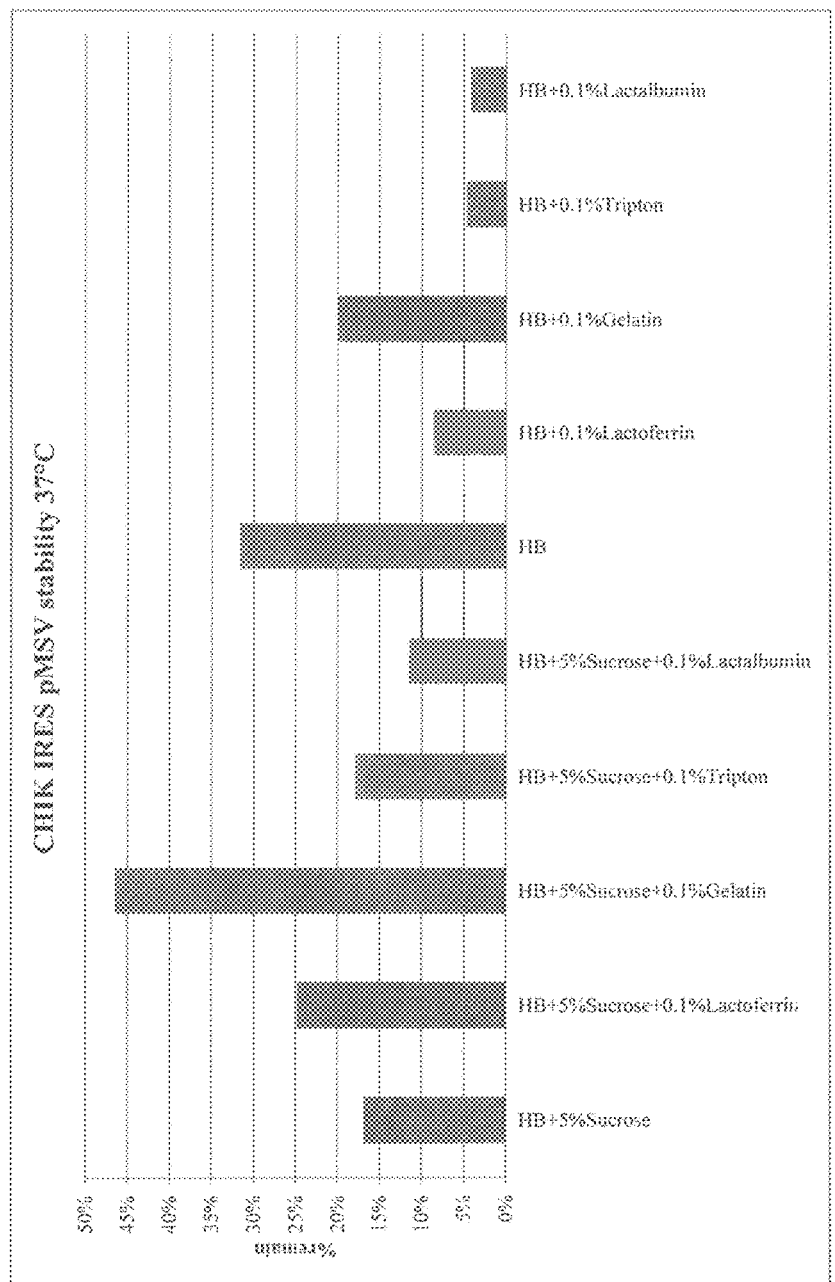
FIG. 4 represents an exemplary histogram of experiments using various compositions for testing the stability of exemplary attenuated Alphavirus compositions at 37° C.

In other exemplary methods, different protein agents were analyzed for increased stability of alphavirus formulations compared to controls, without protein or with against other proteins. Compositions containing HB or HBS with target protein agents were analyzed. After incubation (37° C. for ~21 hrs) of about $10^5$ per experimental condition of the attenuated CHIK vaccine composition, aliquots were removed and titrated for growth in Vero cells by $TCID_{50}$. Then, the percentage of remaining virus titer was assessed. As illustrated in FIG. 4, the addition of gelatin to the formulations with or without carbohydrate increased alphavirus vaccine stability at 37° C. (see FIG. 4).

FIG. 4 represents an exemplary histogram illustrating the percent total of CHIK virus titer remaining after incubation in compositions containing HEPES Buffered Saline and a protein, such as Lactoferrin, Tripton, Lactalbumin, and Gelatin, for ~21 hours at 37° C. Among all tested compositions, the composition containing Gelatin and HB buffer demonstrated increased stability by reducing degradation of the alphavirus at room temperature on vaccine stability. The effect was observed to be more than additive when a carbohydrate such as sucrose was included in the composition.

Significant increase in stability of the alphavirus vaccine as compared to the vaccine stored in culture medium containing FBS or PBS alone was observed. One exemplary formulation which produced a very stabile virus vaccine was determined to be a HEPES buffer, sucrose and gelatin formation. Including recombinant gelatin in the formulation, greatly decreased the lability of this alphavirus vaccine.

Example 4

Long Term Stability Study

In some exemplary methods, a concentration range of gelatin was analyzed to determine which concentration of gelatin had the best stabilizing property for an alphavirus composition. In one method, two concentrations of gelatin were selected for combinatory use with HBS (HBS+0.5% and HBS+1% Gelatin) in certain compositions. Then, a long term stability study evaluating the liquid CHIK vaccine at 4° C. or −80° C. was conducted (Table 1) with compositions containing Gelatin and HBS. Examples of these compositions are provided below.

Exemplary Compositions:
1. HB—HEPES Buffer Saline 15 mM HEPES and 150 mM NaCl
2. HBS—HEPES Buffer Saline with 5% Sucrose
3. HSG (0.5% Gelatin)—HEPES Buffer Saline with 5% Sucrose and 0.5% Gelatin
4. HSG (1% Gelatin)—HEPES Buffer Saline with 5% Sucrose and 1% Gelatin

TABLE 1

| Long Term Stability Study Designs | | | | | | | | |
|---|---|---|---|---|---|---|---|---|
| weeks | 0 | 1 | 3 | 4 | 8 | 12 | 24 | 36 |
| 4° C. | x | x | x | x | x | x | x | x |
| −80° C. | x | x | x | x | x | x | x | x |

Vaccine samples formulated in these compositions were stored in 500 μL volume into 1.5 mL MCT. 15 samples were stored in 4° C. (Micro Climate Chamber; Model# MCB-12-33-33-H/AC) and 15 samples were stored in −80° C. (Thermo; Model# ULT2186-6-D43) per formulation.

Figure 5:
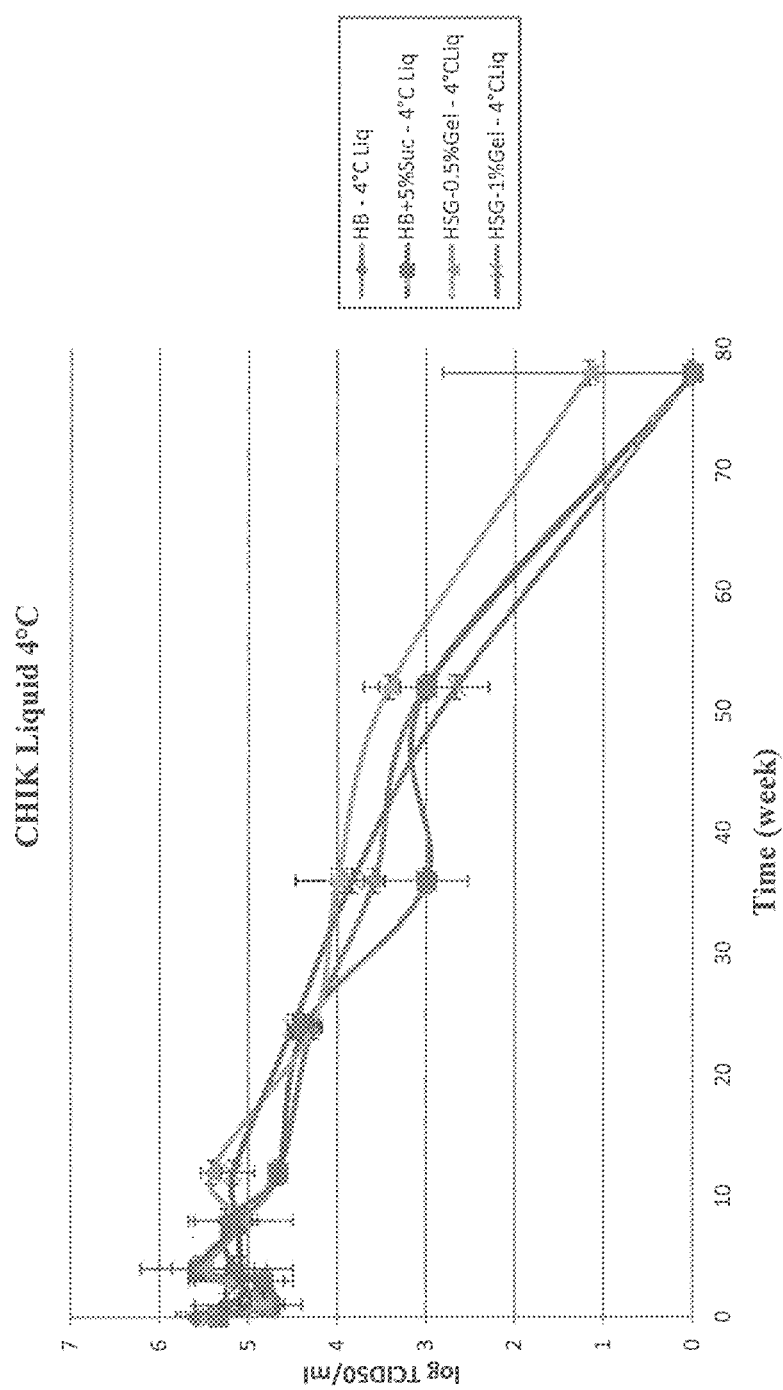
FIG. 5 represents an exemplary graph plotting data from experiments using various liquid compositions for testing the stability of exemplary attenuated Alphavirus compositions at 4° C.
Figure 6:
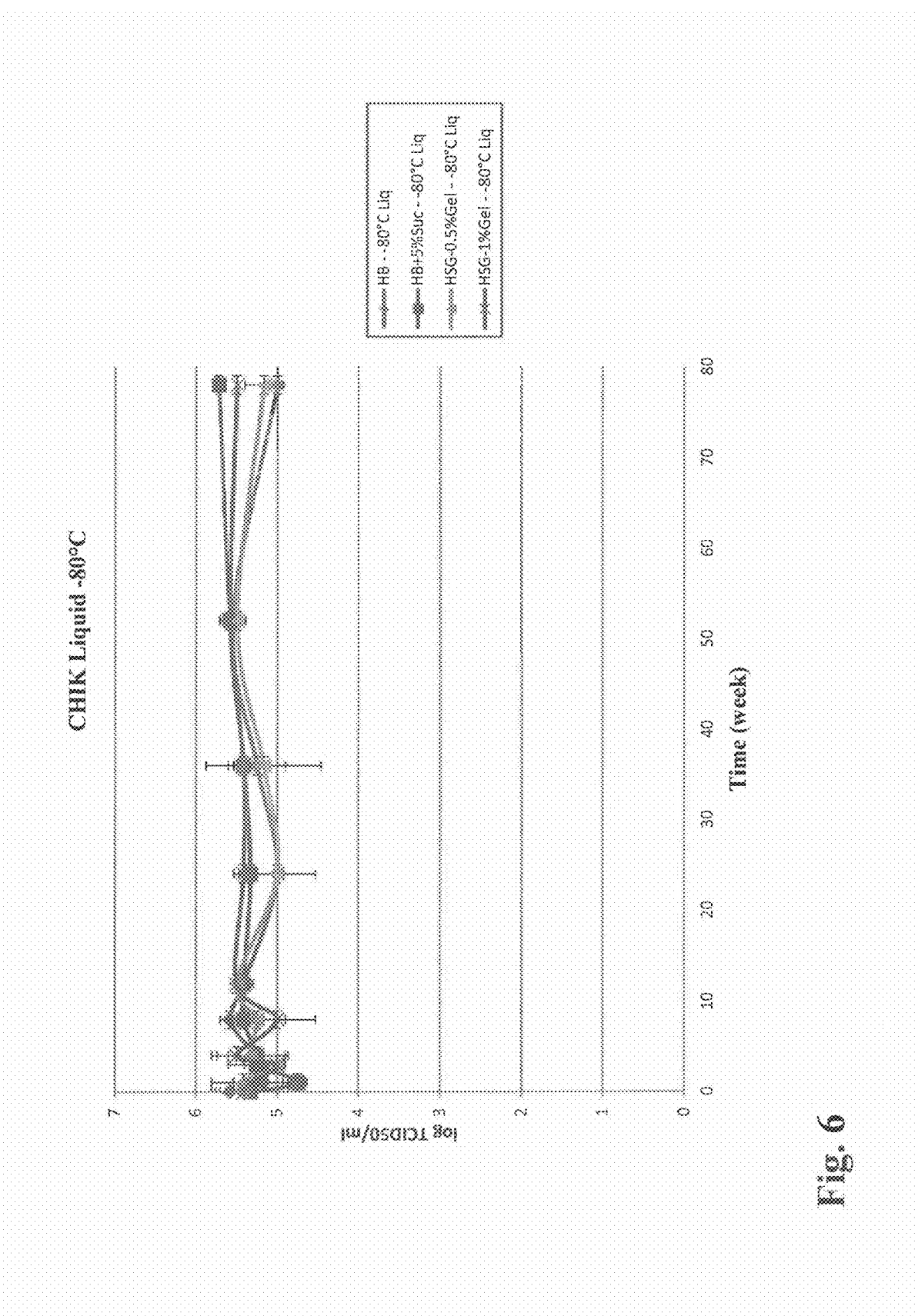
FIG. 6 represents an exemplary graph plotting data from experiments using various liquid compositions for testing the stability of exemplary attenuated Alphavirus compositions at −80° C.

Samples were taken for potency evaluation at the time points indicated in Table 1 and FIGS. 5-6. Samples incubated at 4° C. (FIG. 5) were analyzed in parallel with samples incubated at −80° C. (FIG. 6) to demonstrate the trend of the titer over 36 weeks. As illustrated in the graphs in FIG. 5, vaccines formulated in these compositions had significantly reduced titer loss up to week 12 at 4° C. After incubation for 24 weeks, loss of 1 $\log_{10} TCID_{50}$ or more of the virus titer was observed. The addition of gelatin demonstrated significant positive effects on stabilization of alphavirus vaccine formulation (attenuated CHIK). The alphavirus composition was stable at −80° C. in all compositions tested for the duration of the study (FIG. 6).

Example 4

Lyophilized Formulations

Figure 7:
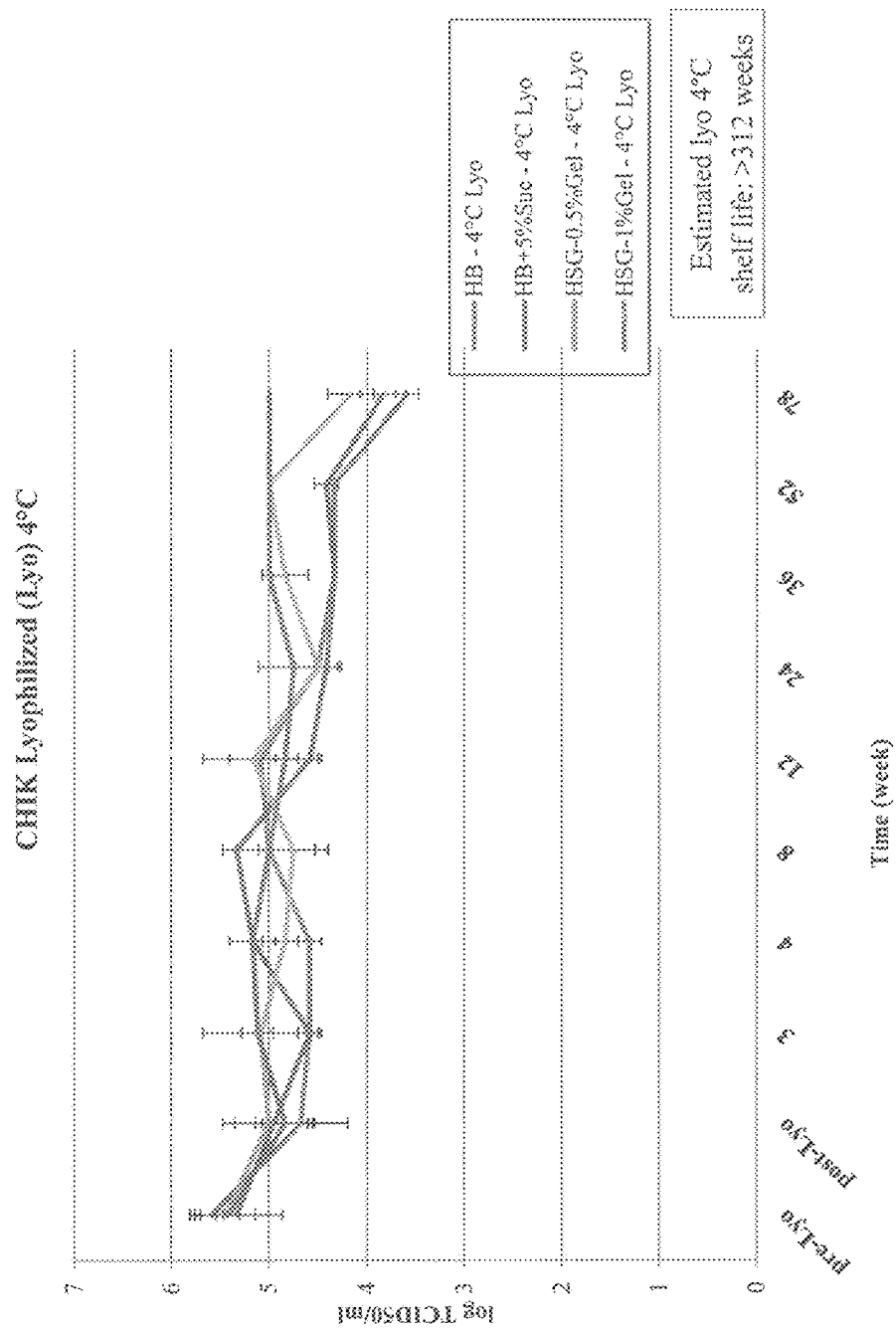
FIG. 7 represents an exemplary graph plotting data from experiments using various lyophilized compositions for testing the stability of exemplary attenuated Alphavirus compositions at 4° C.
Figure 8:
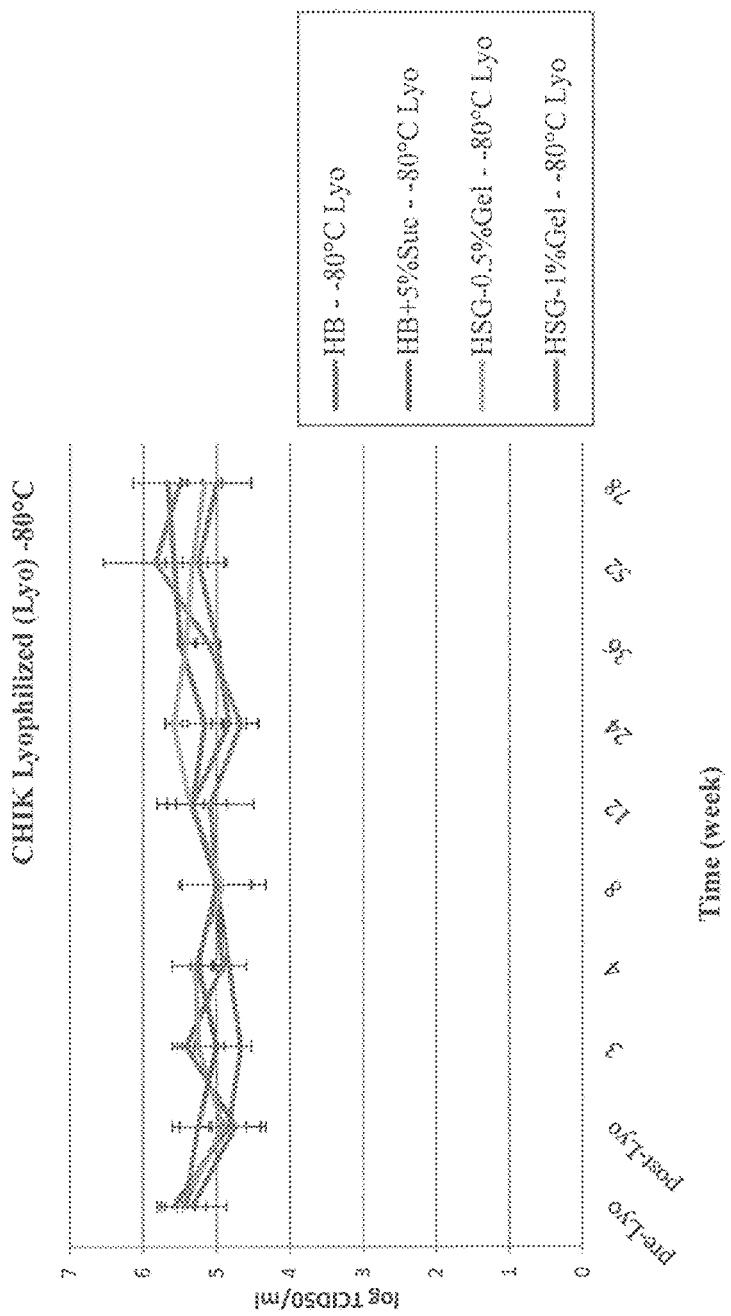
FIG. 8 represents an exemplary graph plotting data from experiments using various lyophilized compositions represents an exemplary histogram of exemplary attenuated Alphavirus compositions at −80° C.

In another exemplary method, long term stability of a lyophilized attenuated alphavirus formulation (e.g. CHIK vaccine formulation) were evaluated. The lyophilized vaccine formulations were stored at 4° C. (FIG. 7) or −80° C. (FIG. 8). Samples taken at the indicated time points were reconstituted and titrated in Vero cells by $TCID_{50}$. The exemplary attenuated CHIK vaccine formulated in HSG (both 0.5% and 1% Gelatin) demonstrated minimal loss of virus titer for greater than 80 weeks at 4° C. while HB or HBS composition lost about 1 $\log_{10} TCID_{50}$ of the virus titer after 24 weeks (FIG. 7). The CHIK vaccine was very stable at −80° C. in all compositions tested for the duration of 80 weeks and more (FIG. 8).

In one other exemplary method, Gelatin from different sources was compared for the ability to stabilize the CHIK vaccine. No differences were observed (FIG. 9) between any manufacturers including Sigma, Merck, Tekni and Gelita.

FIGS. 5-6 represent exemplary graphs demonstrating increased stability of the liquid an attenuated alphavirus vaccine formulation (e.g. CHIKV) stored in compositions containing HB, HBS or HSG for up to 80-90 weeks at 4° C. (FIG. 5) or at −80° C. (FIG. 6). FIGS. 7-8 represent exemplary graphs demonstrating potency of the CHIKV vaccine lyophilized in compositions containing HB, HBS or HSG for 80-90 weeks at 4° C. (FIG. 7) or at −80° C. (FIG. 8).

Figure 9:
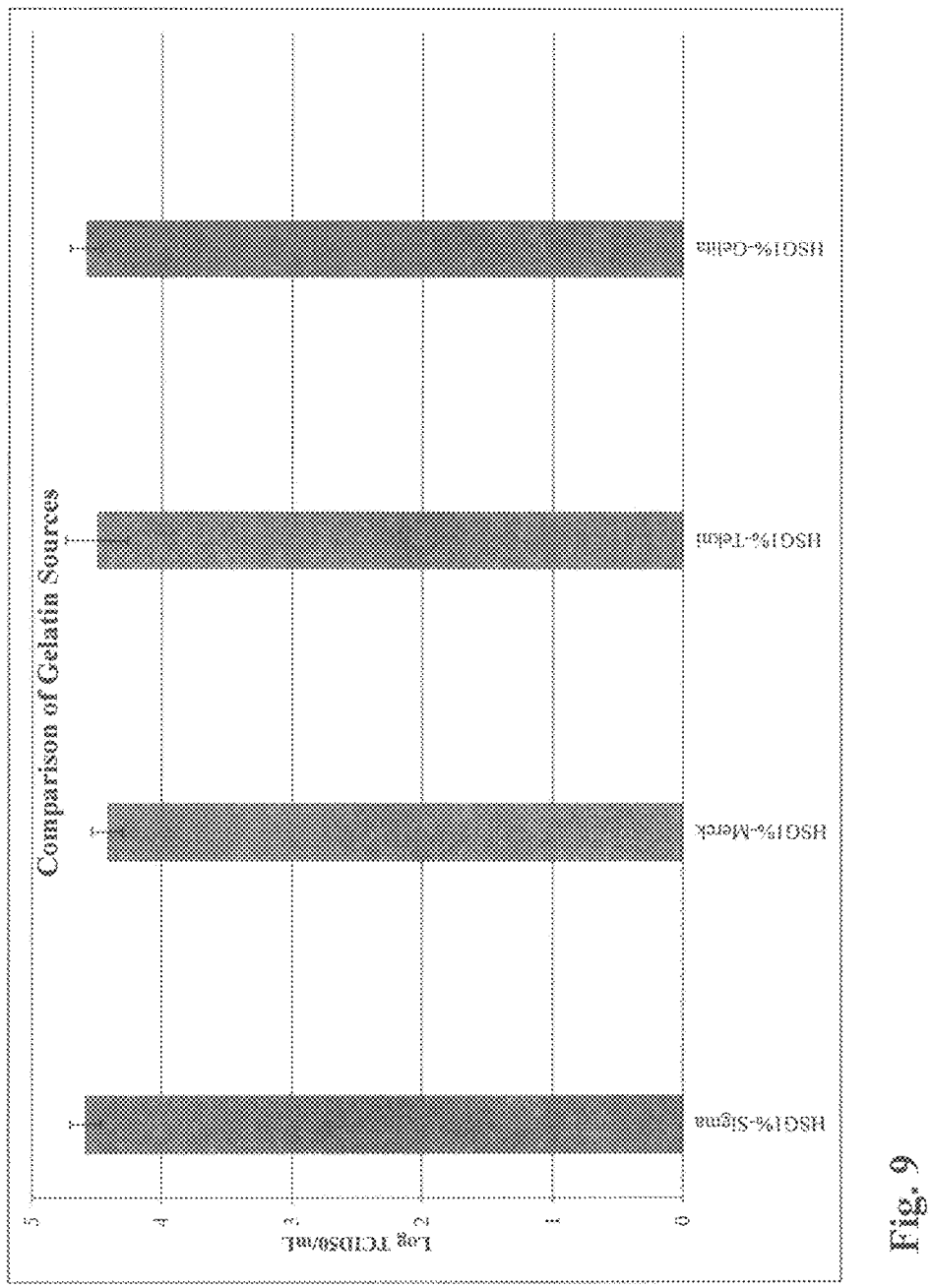
FIG. 9 represents an exemplary histogram of experiments using various compositions having different gelatin formulations for testing the stability of exemplary attenuated Alphavirus compositions.

FIG. 9 provides an exemplary histogram comparing effect of Gelatin from different sources on stabilizing the CHIK vaccine.

Figure 10:
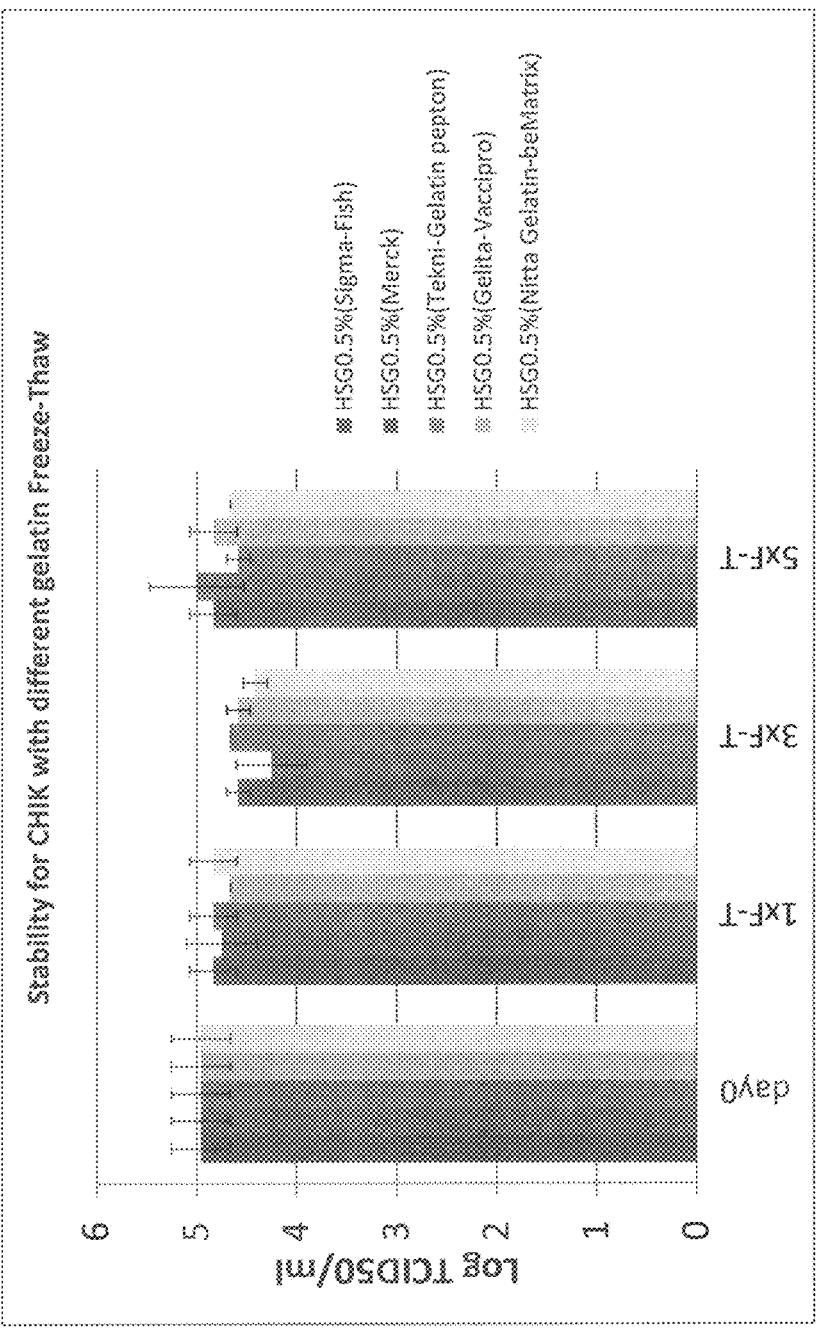
FIG. 10 represents an exemplary histogram of experiments using various compositions having different gelatin formulations for testing the stability of exemplary attenuated Alphavirus compositions after freeze-thaw treatment.

FIG. 10 represents an exemplary histogram plot comparing effects of gelatin from different sources on CHIK vaccine stability after freeze-thaw (F-T) treatment. CHIK vaccine compositions include HEPES (HS) buffer with 0.5% gelatin. Gelatins from five different sources were tested including Sigma, Merck, Tekni, Gelita, and Nitta. CHIK vaccine compositions were exposed to one (1×), three (3×), or five (5×) rounds of F-T treatment. No significant differences were observed among the different sources of gelatin. Therefore, this data supports that any source of gelatin (e.g. capable of being introduced to a subject, such as a pharmaceutical grade) can be used in the instant formulations to increase stability of the live, attenuated virus in the compositions disclosed herein.

Figure 11:
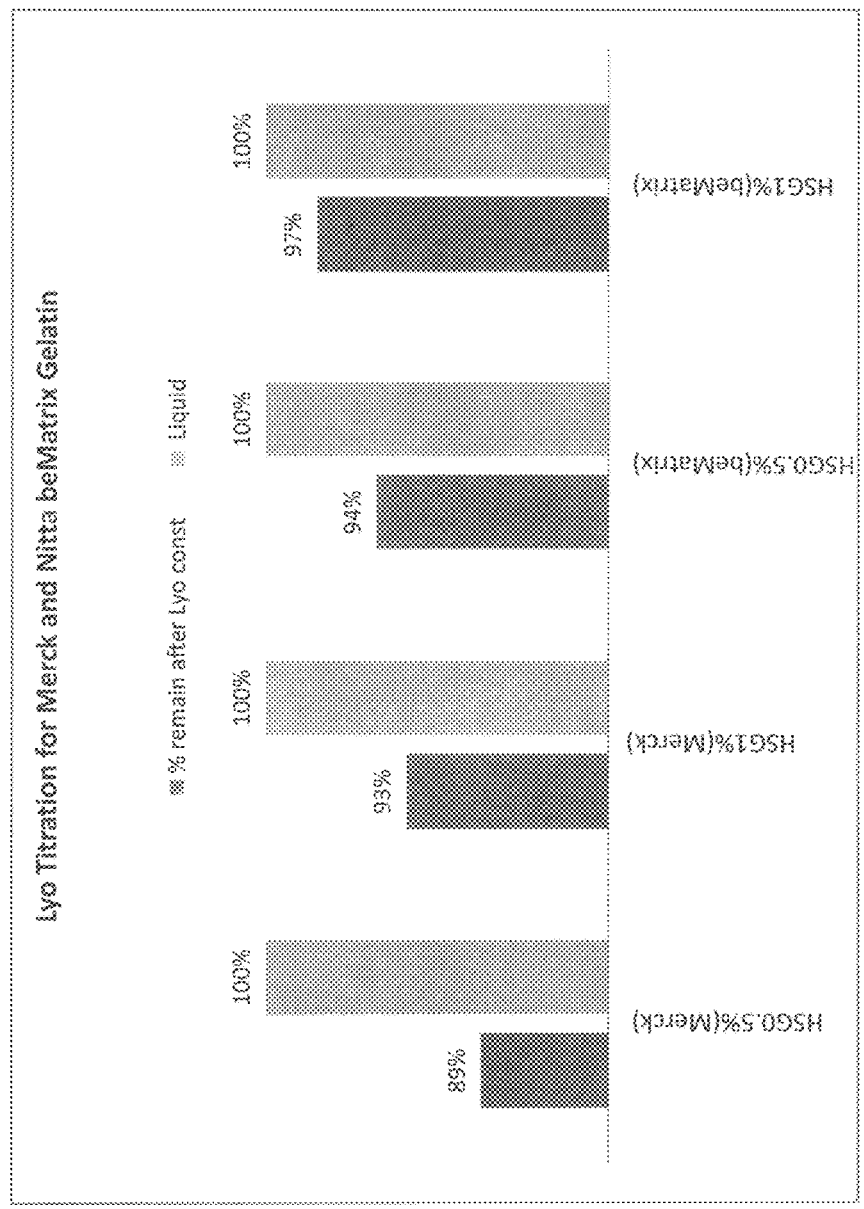
FIG. 11 represents an exemplary histogram of experiments using various compositions having different gelatin formulations for testing the stability of exemplary attenuated Alphavirus compositions after lyophilization.

FIG. 11 illustrates an exemplary histogram plot comparing effect of gelatin from different sources on CHIK vaccine stability after lyophilization, as compared to liquid cultures. CHIK vaccine compositions include HEPES (HS) buffer with either 0.5% or 1.0% gelatin. Gelatin from Merck and Nitta (beMatrix) were tested. No significant differences were observed between gelatin from Merck and Nitta. Both CHIK vaccine compositions produced a stable lyophilized cake, which retained a significant titer after reconstitution from lyophilization compared to liquid formulations.

TABLE 2

| List of Abbreviation | |
|---|---|
| CHIKV | Chikungunya Virus |
| $TCID_{50}$ | 50% Tissue Culture Infective Dose |
| HB | Hepes Buffer Saline |
| HBS | Hepes Buffer Saline + Sucrose |
| HSG | Hepes Buffer Saline + Sucrose + Gelatin |
| IRES | Internal Ribosomal Entry Site |
| DMEM | Dulbecco's modified minimal essential medium |
| MCT | Microcentrifuge Tubes |
| PBS | Phosphate Buffered Saline |
| FBS | Fetal Bovine Serum |
| Pre-MVS | Pre-Master Virus Seed |

Materials and Methods

Individual aliquots of a predetermined dose of CHIK-IRES vaccine (pre-MVS) were formulated in compositions containing buffers including Hepes buffered saline (HB), Hepes Buffered Saline containing sucrose (HBS), Hepes Buffered saline containing sucrose and gelatin (HSG) at varying concentrations of gelatin (e.g. 0.5% and 1% Gelatin). Formulated hydrated or liquid vaccine was incubated at certain temperatures such as room temperature 37° C., frozen 4° C. or flash frozen, −80° C. Samples were taken from these formulations at predetermined intervals, and titrated for the presence of infectious virus by $TCID_{50}$ in for example, 96 well plates with Vero cells.

Cell Lines and Tissue Culture

A research-grade Vero cell bank derived from the applicant's cGMP Working Cell Bank was prepared to perform these experiments. Vero cells were obtained: Vero (WHO) Working Cell Bank passage:142 (lot#INV-VERO-WCB-001; $5 \times 10^6$), and was stored in liquid nitrogen. A vial was rapidly thawed in a water bath and directly inoculated into pre-warmed cDMEM (Dulbecco's modified minimal essential medium), about 19 mls containing penicillin-streptomycin, 40 mM L-glutamine and 10% FBS) in a T-75 $cm^2$ flask and incubated at 37° C., 5% $CO_2$. Cells were allowed to grow to confluency, and subcultured using PBS, Trypsin (HyClone, for example, cat#SH30042.01) and cDMEM-10. This flask was expanded to two T-185 $cm^2$ flasks and grown until the cells reached 100% confluency. Cells were harvested by trypsinization, centrifuged at 800×g for 10 minutes, and resuspended in DMEM containing 20% FBS and 10% DMSO at a concentration of $1\times10^7$ cells/mL. These cells (20 mL total) were aliquoted into cryovials (20×1 mL) and labeled: Vero WHO WCB p#142-2 (Waisman) (WWCB) 1 ml $1\times10^7$ cells/mL, 13Jan12 LV and stored in liquid nitrogen.

Vero $WWCB_I$ WHO cells were grown and maintained in Dulbecco's modified minimal essential medium (DMEM) containing penicillin-streptomycin and 10% FBS (HyClone) (DMEM-10%-FBS). Trypsin was used to maintain cells. Two days before viral adsorption, 96-well plates were plated with $1.4\times10^5$ cells/mL in 100 uL per well of DMEM-FBS-10%. Incubators were monitored daily to maintain indicated temperatures. Virus dilutions, adsorption and TCID50 assays were performed in cDMEM-FBS 2%.

CHIK Attenuated Virus

Molecular generation of CHIK vaccine used in various methods described is designated CHIK-002 (previously described). CHIK vaccine was generated and propagated in Vero cells. A pre-Master Virus seed stock was used for these experiments at a concentration of $10^5$ $TCID_{50}$/mL. Briefly, the CHIK pre-MVS was generated after infection of monolayers of Vero cells. Vaccine-virus is secreted into the supernatant, and the virus is harvested from the medium after clarification/removal of the dead Vero cells. The CHIK-pre-MVS was stabilized in DMEM containing 10% FBS, and stored at −80° C.

Assay Method $TCID_{50}$ assay methods were used to quantify the amount of infectious virus present (potency or stability) in the vaccine preparations. $TCID_{50}$ is defined as the level of dilution of a virus at which half of a series of replicates of infected wells in the 96-well plate shows signs of virus infectivity, as evidenced by for example, CPE (Cytopathic Effect). Vero cells ($WWCB_I$ WHO) were grown and maintained in Dulbecco's modified minimal essential medium (DMEM) containing penicillin-streptomycin, L-glutamine and 10% FBS (HyClone) (DMEM 10%-FBS). Aliquots of the formulated samples were rapidly thawed in a water bath and mixed. An initial dilution of pre-MVS into a working concentration was performed, and ten-fold dilution series of these samples were made in for example, cDMEM-2% FBS in 96-well plates. Diluted viruses were maintained at 4° C. prior to inoculation of the Vero cell monolayers. At the time of assay, the growth medium was aspirated from the 96-well plate, and 100 μL of each virus dilution was added to the wells. The plates were incubated for 3-5 days at 37° C. and 5% $CO_2$. Titer was calculated using the Spearman-Karber method.

Vaccine Formulations

Stability experiments were prepared with vaccines including research-grade vaccine preparations, and the CHIK-IRES pMVS derived at Inviragen. For screening of excipients and stability studies using various compositions provided herein, vaccine formulations were prepared in a final volume of 500 μL containing $10^5$ $TCID_{50}$/mL virus per sample. Samples were prepared in bulk in indicated buffers/formulations and input samples were taken before the study was initiated as a measure of initial titer. Samples were aliquoted into MCT and stored for the indicated time and temperature. Each of the four formulations were prepared for 500 μL final with $10^5$ TCID50/mL virus per sample. 60 samples per formulation were prepared in bulk and input samples were taken before they were aliquotted into 1.5 mL MCT containing 500 uL.

Formulated Vaccine Storage

Vaccine formulations were stored at 4° C. (Micro Climate Chamber; Model# MCB-12-33-33-H/AC) and at −80° C. (REVCO Elite Plus; Model# ULT2186-6-D43). Both systems were monitored with Dickson Wizard2—900 MHZ Logger (Model#WT-220 for 4° C. and WT-240 for −80° C.).

All of the COMPOSITIONS and METHODS disclosed and claimed herein can be made and executed without undue experimentation in light of the present disclosure. While the compositions and methods have been described in terms of preferred embodiments, it is apparent to those of skill in the art that variations maybe applied to the COMPOSITIONS and METHODS and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

What is claimed is:

1. A live, attenuated alphavirus virus composition comprising:

one or more live, attenuated alphaviruses, wherein the live, attenuated alphaviruses are selected from the group consisting of chikungunya (CHIK) virus, o'nyong'nyong virus, Eastern equine encephalitis, Western equine encephalitis, and Venezuelan equine encephalitis;

10.0 mM to 20.0 mM HEPES buffer;

one or more carbohydrate agents having a concentration from 1.0% to 15% (w/v) selected from the group consisting of: trehalose, sucrose, mannitol, sorbitol, and galactose; and 0.1% to 1.0% (w/v) gelatin but does not contain human serum albumin (HSA), wherein the composition stabilizes the live attenuated alphaviruses.

2. The virus composition of claim 1, wherein the live, attenuated alphaviruses are chikungunya (CHIK) viruses.

3. The virus composition of claim 1, wherein the composition is in aqueous form.

4. The virus composition of claim 1, wherein the carbohydrate comprises sucrose.

5. The virus composition of claim 1, wherein the gelatin concentration is 0.5% to 1.0% (w/v).

6. The virus composition of claim 4, wherein the HEPES buffer concentration is 15 mM; and the gelatin concentration is from 0.5% to 1.0% (w/v).

7. The virus composition of claim 1, wherein the HEPES buffer concentration is 15 mM.

8. The virus composition of claim 1, further comprising salt.

9. A method for decreasing inactivation of a live, attenuated alphavirus composition comprising, combining one or more live attenuated alphaviruses, wherein the live, attenuated alphaviruses are selected from the group consisting of chikungunya (CHIK) virus, o'nyong'nyong virus, Eastern equine encephalitis, Western equine encephalitis, and Venezuelan equine encephalitis, with a composition comprising: 10.0 mM to 20.0 mM HEPES buffer; one or more carbohydrate agents at a concentration of 1.0% to 15% (w/v) selected from the group consisting of: trehalose, sucrose, mannitol, sorbitol, and galactose; and gelatin having a concentration of 0.1% to 1.0% (w/v) but does not contain human serum albumin (HSA), wherein the composition decreases inactivation of the live, attenuated alphaviruses.

10. The method of claim 9, further comprising partially or wholly dehydrating the combination.

11. The method of claim 9, further comprising partially or wholly re-hydrating the composition prior to administration.

12. The method of claim 9, wherein the composition increases the shelf-life of an aqueous virus composition.

13. The method of claim 9, wherein the HEPES buffer concentration is 15 mM; and the gelatin concentration is from 0.5% to 1.0% (w/v).

14. The method of claim 9, wherein the live, attenuated alphavirus composition is formulated for use as a medicament for administration to a subject to induce an immune response against alphavirus in the subject.

15. A kit for decreasing the inactivation of a live, attenuated alphavirus composition comprising:
at least one container;
a composition comprising 10 mM to 20 mM HEPES buffer;
one or more carbohydrate agents at a concentration of 1.0% to 15% (w/v) selected from the group consisting of:
trehalose, sucrose, mannitol, sorbitol, and galactose; and
0.1% to 1.0% (w/v) gelatin but does not contain human serum albumin (HSA); and
an alphavirus,
wherein the alphaviruses are selected from the group consisting of chikungunya (CHIK) virus, o'nyong'nyong virus, Eastern equine encephalitis, Western equine encephalitis, and Venezuelan equine encephalitis.

* * * * *